United States Patent
Riesinger (10) Patent No.: US 10,231,877 B2
(45) Date of Patent: Mar. 19, 2019

(54) WOUND-COVERING ARTICLE WITH PREPARATION FOR ATTACHMENT OF A VACUUM DEVICE

(71) Applicant: Birgit Riesinger, Munster (DE)

(72) Inventor: Birgit Riesinger, Munster (DE)

(73) Assignee: BSN medical GmbH, Hamburg (DE)

( * ) Notice: Subject to any disclaimer, the term of this patent is extended or adjusted under 35 U.S.C. 154(b) by 0 days.

(21) Appl. No.: 14/096,856

(22) Filed: Dec. 4, 2013

(65) Prior Publication Data
US 2014/0163486 A1 Jun. 12, 2014

Related U.S. Application Data

(63) Continuation of application No. PCT/EP2012/060697, filed on Jun. 6, 2012.

(30) Foreign Application Priority Data

Jun. 7, 2011 (DE) .................. 10 2011 050 884
Jan. 5, 2012 (DE) .................. 10 2012 100 073
Mar. 7, 2012 (DE) .................. 10 2012 101 906

(51) Int. Cl.
- *A61F 13/02* (2006.01)
- *A61M 1/00* (2006.01)
- *A61F 13/00* (2006.01)

(52) U.S. Cl.
CPC .... *A61F 13/0243* (2013.01); *A61F 13/00063* (2013.01); *A61M 1/0086* (2014.02); *A61M 1/0088* (2013.01)

(58) Field of Classification Search
CPC .................. A61F 13/0243; A61M 1/0088
See application file for complete search history.

(56) References Cited

U.S. PATENT DOCUMENTS

| 6,116,782 A * | 9/2000 | Arkins ................. B32B 27/08 383/202 |
| 2002/0114543 A1* | 8/2002 | Murray .............. B65D 75/5894 383/202 |
| 2005/0258222 A1* | 11/2005 | Hewitt ................. B65D 77/28 229/103.1 |
| 2008/0208171 A1 | 8/2008 | Argenta et al. ............ 604/540 |
| 2008/0306456 A1* | 12/2008 | Riesinger ............ A61F 13/0203 604/316 |
| 2009/0312723 A1* | 12/2009 | Blott et al. ................... 604/290 |
| 2009/0326496 A1* | 12/2009 | Court ....................... A61L 15/60 604/368 |

(Continued)

FOREIGN PATENT DOCUMENTS

| DE | 2953373 | 6/1978 | ............. A61F 13/00 |
| DE | 202006007877 | 8/2006 | ............. A61F 13/00 |

(Continued)

OTHER PUBLICATIONS

Wound Gels/Gel Dressings: Product Safety Data Sheet. Smith and Nephew: Apr. 17, 2013.*

*Primary Examiner* — Benjamin Klein
*Assistant Examiner* — Sara Sass
(74) *Attorney, Agent, or Firm* — Rankin, Hill & Clark LLP (57) ABSTRACT

The present invention relates to a wound-covering article (10) having a film-like element (11) of reduced gas permeability, wherein said film-like element has a preparation (12) for attachment of a vacuum device.

11 Claims, 8 Drawing Sheets

(56) References Cited

U.S. PATENT DOCUMENTS

2010/0324516 A1* 12/2010 Braga ................ A61F 13/00
                                                          604/378
2012/0312734 A1* 12/2012 Kalayci et al. ............. 210/490

FOREIGN PATENT DOCUMENTS

| DE | 102010006273 | 1/2010 | ............ A61M 1/00 |
| EP | 1814609 | 2/2005 | ............ A61M 1/00 |
| EP | 2004116 | 11/2007 | ............ A61F 13/00 |
| EP | 2098257 | 12/2009 | ............ A61M 1/00 |
| WO | WO 2001-052780 | 7/2001 | ............ A61F 5/44 |
| WO | WO 2003-094813 | 11/2003 | ............ A61F 13/02 |
| WO | WO 2006-056294 | 6/2006 | ............ A61M 1/00 |
| WO | WO 2007-051599 | 5/2007 | ............ A61F 13/00 |
| WO | WO 2009-071933 | 6/2009 | ............ A61M 1/00 |
| WO | WO 2009-124125 | 10/2009 | ............ A61F 5/01 |
| WO | WO 2010-094957 | 8/2010 | ............ A61M 1/00 |
| WO | WO 2012-168298 | 12/2012 | ............ A61M 1/00 |

* cited by examiner

WOUND-COVERING ARTICLE WITH PREPARATION FOR ATTACHMENT OF A VACUUM DEVICE

CROSS-REFERENCE TO RELATED APPLICATIONS

The present invention is a continuation and claims priority under 35 U.S.C. § 120 and § 365(c) to PCT International Patent Application PCT/EP2012/060697, filed Jun. 6, 2012, which claims priority to German Patent Application No. 10 2011 050 884.8, filed Jun. 7, 2011 and German Patent Application No. 10 2012 100 073.5, filed Jan. 5, 2012 and German Patent Application No. 10 2012 101 906.1, filed Mar. 7, 2012, all of which are herein incorporated by reference in their entireties.

BACKGROUND

The present invention relates to a wound-covering article with prearrangement for attachment of a vacuum device in accordance with the generic part of claim 1.

Wound drainage systems for the treating of heavily exuding wounds, in particular in the case of edemas, are generally known. The individual components can vary as a function of the entire system, whereby the general construction remains substantially the same. Core components are a gas- and fluid-tight wound covering and a means generating a vacuum, e.g., a vacuum pump. In this manner substances present in the wound can be evacuated via a drainage hose that must be arranged under the wound-covering element.

Such drainage devices for the treatment of wounds are known, e.g., from the patent EP 1 814 609 B1. The device comprises an absorption body with super-absorbing particles that is placed in the wound area. A gas-tight, film-like wound-covering element is adhesively fastened on the body of the patient over it. A drainage hose is introduced into the wound area parallel to the wound-covering element via which hose the substances present in the wound area can be evacuated.

A device for wound treatment using a vacuum is also known from DE 29 53 373 C2 that is built up from a wound-covering element, a foam insert located underneath it and from at least one hose line communicating with the pores of the foam insert.

Other wound drainage systems with vacuum pumps attached to them are sufficiently known from the prior art. Such wound drainage systems are, as previously described, very complex in their construction, have expensive individual components and are difficult to manage in their use. In particular, the wound-covering elements used in them must be able to meet the special requirements for such a vacuum system and are therefore often associated with elevated costs.

Therefore, the present invention has the problem of making available a wound-covering article for use in a vacuum system that is simple and flexible in its use and requires only low manufacturing costs.

DETAILED DESCRIPTION OF THE INVENTION

This problem is solved by the wound-covering article in accordance with the main claim. Other preferred embodiments are reproduced by the features of the dependent claims.

Accordingly, the present invention discloses a wound-covering article that comprises a film-like element with reduced gas permeability, whereby this film-like element comprises a prearrangement for attaching a vacuum device.

The term "film-like" means that the material of the wound-covering article can be flexibly adapted to the body of the patient and is generally suited for being used in wound care. In particular, a film consisting of polyethylene, polypropylene or polytetrafluoroethylene or a fabric or fleece that has a reduced gas permeability, for example, a polypropylene fleece with an almost gas-tight layer such as, e.g., polyurethane is suitable. In this connection "reduced gas permeability" means that the wound-covering article does not obligatorily have to be absolutely gas-tight but upon the optional attachment of a vacuum device it resists the vacuum and appropriate fluids from the wound can be evacuated underneath the wound-covering element. The film-like element can accordingly also be perforated in as far as it continues to meet the requirements for an attached vacuum system.

In this connection is it essential for the wound-covering article of the invention that it can be used passively, i.e., as a pure wound-covering element, as well as actively, i.e., in combination with a vacuum device since the variably designed prearrangement for attaching a vacuum device can be attached at any time. This has the particular advantage that the work can be performed rapidly and in a simple manner in addition to a vacuum only upon an accumulation of wound exudates that has become apparent without having to replace the already applied wound covering. This is especially advantageous in the case of heavily exuding wounds, in particular chronic wounds such as in diabetes, ulcers and similar diseases and makes it possible for the nursing personnel to rapidly and flexibly adapt the necessary care to the healing process of the wound.

In addition, therefore, there is the possibility of selecting the suitable drainage therapy according to the nature of the wound. In the case of wounds in which a relatively slight suction suffices, the wound-covering article can be passively managed. If a relatively higher suction is required for effectively dewatering the wound, a change can be made by connecting a vacuum device to an active operating mode.

These vacuum devices are operated as a rule at an atmospheric pressure of −80 to −150 mm Hg. However, in certain instances a vacuum of −80 mm Hg can result in irritation or even damage, for example, by ischemias. Therefore, it can also be appropriate in this regard not to expose wounds to such a higher suction that do not absolutely require a higher suction in order to be effectively dewatered.

The wound-covering article in accordance with the present invention can develop a hydrodynamic suction of −10 to −100 mm Hg when it is passively used. In particular, the hydrodynamic suction can be around −20, −30, −40, −50, −60, −70, −80 or −90 mm Hg. This suction can be precisely adjusted by dosing the amount of super-absorbing polymers, modified cellulose and/or alginates. Thus, it can be, for example, between 40 wt % and 99 wt % of the wound-covering article. All numeric graduations between these values are to be considered as having been disclosed.

On the one hand, it is advantageous that the developing hydrodynamic suction by itself causes fewer irritations of the tissue and thus, furthermore in the case of wounds that do not necessarily require a rather high suction in order to be effectively dewatered, the irritations accompanying a vacuum therapy can be avoided. At the same time the treatment option remains open that for the case that the wound requires a higher suction at a later point in time, this requirement can be taken into account by connecting in a vacuum device. Inversely, the vacuum device can be decoupled again for the case that the wound requires a lesser suction at a later point in time.

However, even the usage in the active mode has considerable advantages: thus, the atmospheric vacuum exerted by the vacuum device can be adjusted lower than in the case of a vacuum device operated without the wound-covering article in accordance with the invention since in the active mode the hydrodynamic suction and the atmospheric vacuum complement one another. This has positive effects, among other things, on the battery service life and the operating noise. Furthermore, the cited irritations can be avoided by the lower atmospheric vacuum.

"Prearrangement" generally denotes every type of element of the wound-covering article that is suited for attaching a vacuum device to it. The prearrangement for the attaching of a vacuum device can therefore be differently constructed and have one or more of the following constructions:
a) a local thinning of material,
b) a local material recess under or over which a protective element that can be perforated is placed,
b) a local material recess under or over which an adhesive element that can be drawn off is placed,
c) a marking that indicates a possible perforation location,
d) an opening that can be closed with a cover, and/or
e) a flange for a coupling device.

"Local thinning of material" denotes here only a section of material in the film-like element that is thinner than the surrounding material and is therefore easier to divide or to penetrate in order to produce a connection to the vacuum device. A "local material recess under or over which a protective element that can be perforated is placed" designates a round opening or recess formed with a similar shape that is closed with a protective element in that the recess is covered on the bottom or on the top. The protective element is attached for its part to the film-like element and can consist of a material different from the film-like element. All materials are suitable as material for the protective element that allow a ready attachment to vacuum device, in particular a plastic film or also a film coated with aluminum such as is used in a similar form for straw perforation openings in beverage packages. The basic principle is in general very similar to that of beverage packages, namely, the establishing of a connection by perforating the protective element.

Alternatively to the protective elements that can be perforated, a material recess that is covered on the bottom or on the top with an adhesive element that can be drawn off is conceivable. The opening in the film-like element is covered over with an adhesive flap that can be drawn off and that is drawn off as needed. If the adhesive element is placed underneath, it is removed before use so that the opening is free for the attaching of a vacuum device. However, in another variant the adhesive element can also serve as a passage location in order, e.g., to establish a connection to the vacuum device via a cannula. The protective element, that can be perforated, can optionally also be connected to an adhesive element that lies above it and that can be drawn off.

The protective element, that can be perforated, and also the adhesive element, that can be drawn off, can consist of materials similar to those of the film-like element or, however, of paper, a suitable material for membranes or of a composite substance of paper and, for example, a metallic film.

In a simplified form of the prearrangement it has only a marking, that indicates a possible perforating location, on the film-like element and thus is rendered visible. This simple form can also be combined with the previously cited embodiment of the prearrangement.

In another variant the prearrangement has a cover that closes a corresponding opening for the attaching of a vacuum device. The cover can be designed as a single-use article, i.e. it cannot be reused after opening, or, however, it can be multiply used and be designed as a screw cover or pressure cover similar to the ones in plastic containers. In addition, the cover can be connected by a flap to the film-like element so that it is not lost prior to the closing of the opening.

In another variant the prearrangement is a flange for a coupling device so that the vacuum device merely has to be set on the prearrangement and as a result a firm and tight connection is established. Of course, even this variant can be combined with a protective element that can be perforated, but also with other variants of the prearrangement.

In another embodiment of the wound-covering article the film-like element is gas-tight and/or permeable by water vapor. As already mentioned, it is not obligatorily necessary that the wound-covering element is completely impermeable by gas; however, the evacuation of substances from the wound area is supported by a gas-tight, film-like element since the vacuum can be built up better and no gases are drawn in by suction from outside of the wound. However, a reduced permeability for gas is sufficient for optionally evacuating using a vacuum. The permeability for water vapor of the film-like element is only significant if water accumulates in an increased manner in edema tissue and should be able to escape in an unhindered manner before additional evacuation means are connected.

In another embodiment of the wound-covering article the film-like element is transparent at least in sections and/or comprises a window-like, re-closable opening through which material can be removed from the wound area located underneath it or can be inserted into this area. This is particularly interesting if the film-like element is to be used together with an absorption body. Furthermore, the opening can be provided with a cover and therefore be re-closed.

In a preferred embodiment the wound-covering article furthermore comprises an absorption body that for its part comprises a hydro-active polymer preferably selected from the group containing super-absorbing polymers, modified cellulose and/or alginate. The absorption body can be firmly connected to the film-like element or loosely placed into the wound before the actual wound covering takes place.

Several substances can be considered as hydro-active polymers: super-absorbing polymers (SAP) are plastics that are capable of absorbing a multiple of their intrinsic weight—up to 1000 times—of liquids. Chemically, it is a copolymer of acrylic acid (propenoic acid, $C_3H_4O_2$) and sodium acrylate (sodium salt of acrylic acid, $NaC_3H_3O_2$), whereby the ratio of the two monomers to one another can vary. In addition, a so-called core-cross linker, CXL is added to the monomeric solution which linker connects the formed, long-chain polymer molecules to each other at locations by chemical bridges ("cross-links" them). These bridges render the polymer insoluble in water. When water or aqueous saline solutions penetrate into the polymeric particle it swells up and tightens this network on the molecular level so that the water can no longer escape without help. The super-absorbing polymers can be present in the wound care article in the form of a granulate, powder, feed stock, compact, foam, in the form of fibers, a knit fiber fabric, non-woven fiber fabric, fiber fleece and/or a fiber wadding.

In the case of modified cellulose it is preferably derivatives of cellulose, preferably sulfo-alkylated cellulose and its derivatives, preferably cellulose ethylsulfonates, carboxy-alkylated cellulose, preferably carboxymethyl cellulose, carboxymethyl cellulose and/or carboxypropyl cellulose, more complex cellulose derivatives such as sulfoethylcarboxymethyl cellulose, carboxymethylhydroxyethyl cellulose, hydroxypropylmethylcellulose and amidated cellulose derivatives such as carboxymethyl cellulose amide or carboxypropyl cellulose amide. Carboxymethyl cellulose is present in particular in the form of sodium carboxymethyl cellulose and is in trade under the name "Hydrofaser". In hygiene products and wound products the fibers are transferred into a laminar matrix. The fibers are gradually converted into a gel cushion by the absorption of liquid from the wound exudate that contains the liquid and does not release it again. The fibers are built up in such a manner that the wound exudate is absorbed only in the vertical direction. This means that as long as the capacity is sufficient, the exudate does not flow beyond the wound edge. In this manner a wound edge maceration can be effectively prevented.

These hydro-active polymers can also be alginates. Alginates are obtained from the brown algae and are woven into a fibrous piece. Chemically, they are polysaccharides, namely, calcium salts and/or sodium salts of alginic acids. Alginates can absorb up to 20 times their intrinsic weight of liquid whereby the wound exudate is stored in the hollow spaces. The $Ca^{2+}$ ions contained in the alginate grid are exchanged by the $Na+$ ions from the exudate until the degree of saturation of $Na-$ ions has been achieved in the alginate. A swelling up of the wound application occurs and a conversion of the alginate fibers into a gel body by the swelling up of the fibers.

Likewise, these hydro-active polymers can also be hydroxy-terminated methacrylate monomers, comprising hydrogen-nanoparticles, such as 2-hydroxyethylmethacrylate (HEMA) and/or 2-hydroxypropylmethacrylate (HPMA), that are marketed as Altrazeal.

It is provided in another preferred embodiment that the absorption body comprises an amount of ≥40 wt % of super-absorbing polymers. The weight portion of the super-absorbing polymers is especially preferably ≥45, 50, 55, 60, 65 or 70 wt %. Wound care articles with such high weight portions of super-absorbing polymers have an especially high absorption capacity for liquids and can replace, under certain conditions, vacuum wound care systems on the market.

This embodiment is especially advantageous since it has the property that it can be used at first as normal wound application ("passive mode"), for example, to remove wound exudate from the wound bottom in an edematous wound region such as occurs, for example, in the case of an ulcer or decubital ulcer.

If it turns out that the absorption- and drainage potential is insufficient, a vacuum device can be attached via the prearrangement in accordance with the invention for attaching a vacuum device and the embodiment can be further operated as a vacuum wound provision ("active mode") without the wound application having to be replaced, which represents a significant increase in comfort for the patient.

In another preferred embodiment the absorption body comprises at least one laminar element consisting of foam and/or fleece.

The concept "foam" designates an open- or closed-pore foam, preferably of polyurethane. The concept "fleece" designates a textile fabric consisting of individual fibers that, in contrast to woven fabrics, knit fabrics and knit goods, is not manufactured from yarns. Fleeces retain their structural integrity as a rule by the adhesion of the individual fibers to each other. They are also designated as "non-wovens" and are produced, e.g., by filling the fibers. The concept "airlaid" designates a special fleece material consisting of cellulose and polyolefin fibers in which super-absorbing polymers are optionally embedded.

The absorption body can preferably contain a substantially flat absorption body consisting of absorption material consisting of an absorbing fleece with super-absorbing polymers distributed in it. These fibers can be in the form of a granulate, powder, feed stock, compact, foam, in the form of fibers, a knit fiber fabric, non-woven fiber fabric, fiber fleece and/or a fiber wadding.

The absorption body comprises at least one material that is selected from the group containing a mat, in particular consisting of an airlaid consisting of these yarns or fibers of super-absorbing polymers with worked-in, super-absorbing polymers, and/or containing a loose filling of super-absorbing polymers. This airlaid mat can preferably comprise a substantially flat material section of absorption material that consists, e.g., of an absorbing fleece consisting of the cited fibers with super-absorbing polymers distributed in it.

This absorption body is can correspond to the absorbing insert contained in a wound application of the applicant of the present invention, such as is disclosed, for example, in W003094813, WO 2007051599 and W0152780 and distributed under the trade name "sorbion sachet". The disclosed content of the cited publications is attached to their full extent to the disclosed content of this publication.

The absorption body can also form a core in another embodiment that optionally comprises flake-like fibers or yarns of super-absorbing polymers and super-absorbing polymers in granulate form, whereby the granulates are adhered or welded onto the fibers or yarns at several levels, and the granulates are distributed over more than 50% of the entire structural height of at least one section of the core, whereby mingled areas of granulate and fibers are present. The weight component of the super-absorbing polymers can preferably be in the range between 10-25 wt %. Similar constructions are known from traditional incontinence materials and are known as hygienic pads for their padding qualities. A casing can be arranged around this core which casing is arranged in an overlapping manner in areas and covers, e.g., an adhesive seam or part of the latter.

In another embodiment the absorption body can also contain fibers comprising at least one flat layer or can contain yarns of super-absorbing polymers onto which super-absorbing polymers in granulate form are adhered. This results in a preferred embodiment in a construction of the body that has at least three layers, whereby two cover layers surround a layer comprising super-absorbing polymers.

No mixtures of fibers and super-absorbing polymers are present in the plane but rather only both materials, that are fixed and adjacent. The optionally provided several layers can also be physically compressed with each other in a preferred embodiment by rolling, pressing, calendering or by similar methods. In addition, the body can have repeating patterns or streaks such as, e.g., a square pattern, a stamped pattern or the like.

In another embodiment the wound care article comprises an absorption body surrounded by an outer casing, whereby the casing comprises means that is designed and/or selected in such a manner that the casing can be deformed in a purposeful manner at least partially by increasing the volume of the absorption body conditioned by an absorption of liquid. The casing can be at least in sections an integral component of the film-like element.

The absorption body preferably comprises a casing, whereby
a) the absorption body comprises in a top view onto its flat side a surface (F1) that is 3% to 75% smaller in the non-wetted state than the surface (F2) of the casing when it is laid flat, and/or
b) the casing comprises an elastic material at least in sections.

According to option a) the absorption body forms an expansion space that ensures that the absorption body can increase in its volume upon the absorption of liquid and is not limited by the casing.

Option b) ensures that the casing does not oppose the expansion of the absorption body conditioned by the absorption of liquid.

Furthermore, it is ensured in this manner that upon the application of a vacuum—assuming sufficient flexibility—the absorption body can be approached to the bottom of the wound, which is required in particular in the case of deep wounds in order to establish in this manner the contact with the exudate to be absorbed.

Alternatively, it can be provided that also or instead of this the film-like element comprises at least in sections an elastic material with the same advantages as described above.

The pores or meshes of the casing are preferably designed in such a manner that they are smaller than the super-absorber particles. This is especially significant because otherwise super-absorber can drip out of the absorption body and therefore must be retained by the casing.

The size of the super-absorber particles is subject to certain stochastic fluctuations but it can be provided that the pores or meshes of the casing are preferably smaller than the average diameter of these super-absorber particles, especially preferably smaller than the average diameter of the simple or multiple standard deviation of these super-absorber particles.

The pores can preferably have a size, e.g., of 0.05 mm to 1.0 mm, preferably 0.20 mm to 0.50 mm. Furthermore, it can preferably be provided that the pores or meshes are limited by the thread sections or fiber sections, that are approximately arched in section by the casing and face outward with the tops of their arches.

In another embodiment the wound-covering article has a laminar adhesive element on at least one of its edges.

In this manner the article can be applied in an airtight manner on the patient's skin around the wound to be treated. Alternatively, the article can be applied on the patient's skin with the aid of adhesive strips. A physiologically acceptable adhesive such as, e.g., a hydrocolloidal adhesive is preferred as adhesive. Likewise, a silicon adhesive or acrylate adhesive can also be provided.

In another embodiment of the wound-covering article the prearrangement has a spacer for limiting the depth upon the attachment of a vacuum device. The spacer can be, e.g., a toothed ring a few millimeters in size that is worked in underneath the marked prearrangement in order not to further injure the wound or hit the absorption body when the prearrangement is pierced through or divided for attaching a vacuum device. Therefore, depending on the buildup of the entire wound-covering article, the depth at which a wound drainage should start with the aid of the vacuum device is precisely predefined. Another possibility for defining the depth the advance consists in the previously cited using of a coupling element or of a flange. In such systems, that require a precisely fitted form, the height at which the drainage starts after the connection has taken place is already given as such by the system.

In another embodiment the wound-covering article comprises at least one other layer, whereby the material of the layer is selected from the group containing:
a) a wound spacing lattice, preferably three-dimensional,
b) a layer with a high drying potential that drains off liquid,
c) a layer comprising modified cellulose,
d) a layer comprising silver or silver ions, and/or
e) a layer with bonding potential for bacteria.

This layer is preferably arranged on the side facing the wound, for example, under the absorption body that is optionally made ready.

This wound lattice is preferably a three-dimensional wound spacing lattice as described, for example, in EP2004116A1. Such a wound spacing lattice that has a smooth and a rough side not only has a type of valve function for the liquid to be removed but also prevents the wound from becoming granulated in the wound application, which facilitates a non-traumatic change of bandage. Furthermore, such a material is suitable for bonding disease-causing bacteria and it can, if applied on the wound with its rough side, result in a non-traumatic debriding and a separation of undesired biofilms.

Alternatively, the wound spacing lattice can also consist of a silicone net or a silicone lattice.

This moisture-removing layer with high drying potential is, for example, a layer of a material that conducts moisture away similar to sports clothing in order to prevent a maceration in this manner. Such a material can consist, for example, of polyester fibers or of mercerized cotton comprising fibers.

Modified celluloses are, e.g., carboxymethyl celluloses (CMC) and cellulose ether as such a one. Depending on the degree of etherification, a hydrocolloidal matrix can be produced from CMS that serves as an additional protective layer.

In a layer comprising silver or silver ions, in particular the antimicrobial qualities are in the foreground. It has been proven that silver has bacteriostatic qualities that can contribute to the healing of the wound.

A layer comprising a bonding potential for bacteria preferably consists of a hydrophobic material that bonds with the bacterial cell surface by interactions with it. Such layers are, e.g., sufficiently known from chromatographic methods.

In another aspect the present invention relates to a coupling device for attaching a vacuum device to the wound-covering article in accordance with the invention.

This coupling device is constructed in such a manner that it makes it possible to attach a vacuum device via the prearrangement made available by the film-like element of the wound-covering article.

In a preferred embodiment the coupling device comprises at least one element selected from the group containing:
a) a cannula (49*b*) for perforating a protection element and/or a thin area in the material
b) a blade (49*c*) for perforating a protection element and/or a thin area in the material
c) a flange counterpiece (33/43)
d) a coupling (48) that can be adhered on, and/or
e) a vacuum element for the vacuum-supported fastening of the coupling device on the wound-covering article.

As an alternative to the cannula any type of a hollow needle can be used that is suitable for being used in an appropriate coupling device.

The coupling device preferably comprises a blade that is, for example, spring-loaded and when placed on the wound-covering article introduces, by being activated, a slot or a hole in the prearrangement for the attachment of a vacuum device. Alternatively, the blade can be arranged in a dome, for example, a rubber dome so that a slot or a hole can be introduced in the prearrangement for the attachment of a vacuum device by pressing on the dome.

In a flange system a coupling connection takes place, e.g., via a screw closure or bayonet closure.

In the case of a coupling that can be adhered on, the coupling counterpiece is adhered on the corresponding connection unit of the prearrangement on the film-like element. For this, e.g., an adhesive element is used on the film-like element which adhesive element is drawn off with the coupling for establishing the connection so that an opening is freed.

In an alternative embodiment the coupling device itself is already vacuum-supported, i.e., the establishment of a connection takes place with the aid of a vacuum so that a coupling connection to the wound-covering article and the film-like element is produced by the vacuum.

In another aspect the present invention relates to a kit for wound care comprising a wound-covering article as previously described and a coupling device as previously described.

Kit systems have in particular the advantage that they can be made available as a complete system for emergency or care personnel, who do not have to think about the suitable individual components.

In a special embodiment of this aspect the kit system comprises at least one other element selected from the following group:
a) a vacuum pump for producing a vacuum,
b) a hose, preferably a vacuum hose, for attaching the coupling device to the vacuum pump,
c) a filter membrane that makes the passage of gas into the hose possible but prevents the passage of liquid,
d) a non-return valve that prevents a backflow of evacuated liquid,
e) a coupling that makes it possible to decouple the kit from a vacuum pump without losing the vacuum.

This vacuum pump is preferably a miniaturized pump, for example, based on a piezo pump system. As described, the pump is preferably constructed so that it can be removed so that it can be carried by a patient, for example, in his pocket and only has to be connected to the coupling device when required. To this end the wound-covering article can comprise a pressure sensor that signals whether and when it is time to connect the pump and to evacuate air again. This can take place, for example, by a color code on the sensor or by a radio notice that is sent, for example, to the pump.

Alternatively, it can be provided that the vacuum pump is a disposable- or multi-use syringe.

In another aspect the present invention relates to the use of a wound-covering article as previously described, a coupling device as previously described and/or a kit as previously described for the treatment of wounds, in particular deep-seated edemas comprising in particular wounds.

This type of use is preferably used in geriatrics but is also found in postoperative treatments of wounds or edemas.

In another embodiment the use of a wound-covering article takes place as previously described, a coupling device as previously described and/or to a kit as previously described in a vacuum wound care system.

Illustrations

The present invention is explained more precisely by the figures shown and discussed in the following. Note in this regard that the figures are only descriptive in nature and are not intended to limit the invention in any way.

Figure 1:
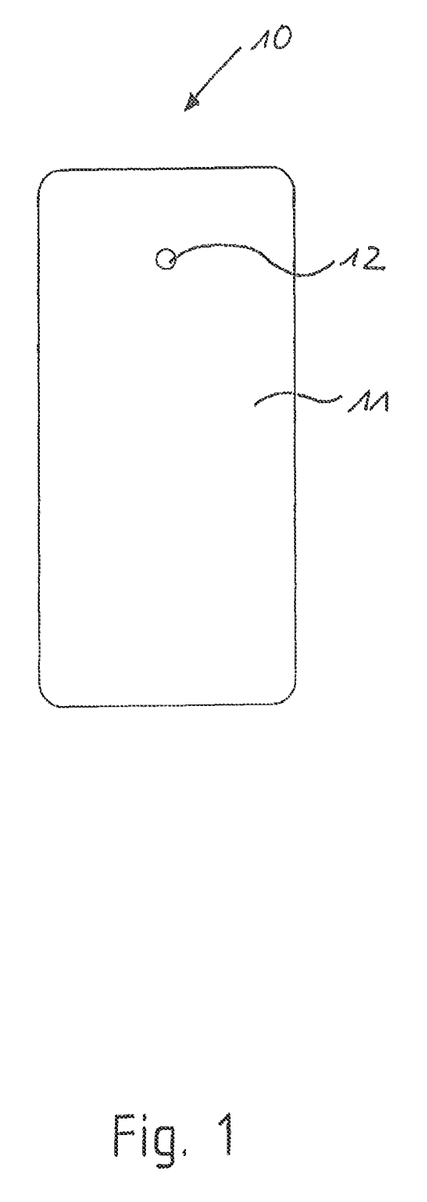

LIST OF REFERENCE NUMERALS 10 wound-covering article
11/31/61 film-like element
12 prearrangement
21/30 adhesive element
22 adhesive strip
32/42 flange
33/43/53 flange counterpiece
34/64 absorption body
35 wound
41/63 material recess
44/62 adhesive element that can be drawn off
45 protective element that can be penetrated
46 protective film
47 adhesive surface
48 coupling that can be adhered on
49b cannula or hollow needle
49c blade
51 cover
52 opening
54 local thinning of material
65 other layer
66 opening in the film-like element
67 cover for removing or introducing the absorption body
71 spacer
72 flange with a protective element that can be perforated
74 adhesive element
80 absorption body
82 elastic casing
83 deep wound
84 wound bottom
85 exudate
86 coupling device FIG. 1 shows the wound-covering article 10 in the simplest "passive form", i.e., with a film-like element 11 that comprises a prearrangement 12 for the attachment of a vacuum device and can also be used as such as a simple wound covering without the attachment of a vacuum device, that is, passively.

Figure 2A:
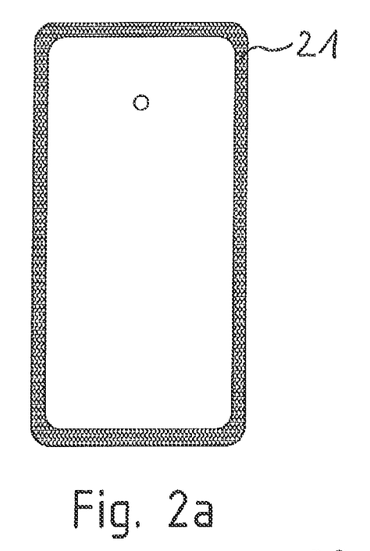
Figure 2B:
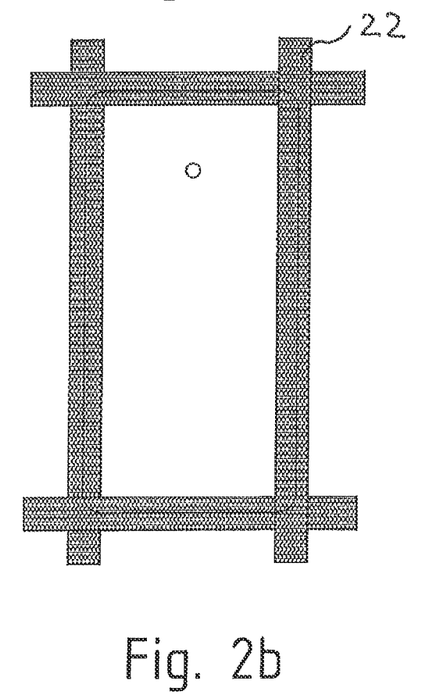

FIG. 2a shows the wound-covering article in the simplest form with an additional adhesive element 21 on the film-like element for positioning on the skin of a patient. FIG. 2b shows the wound care article with adhesive strips 22 around the film-like element for positioning on the skin of a patient.

Figure 3A:
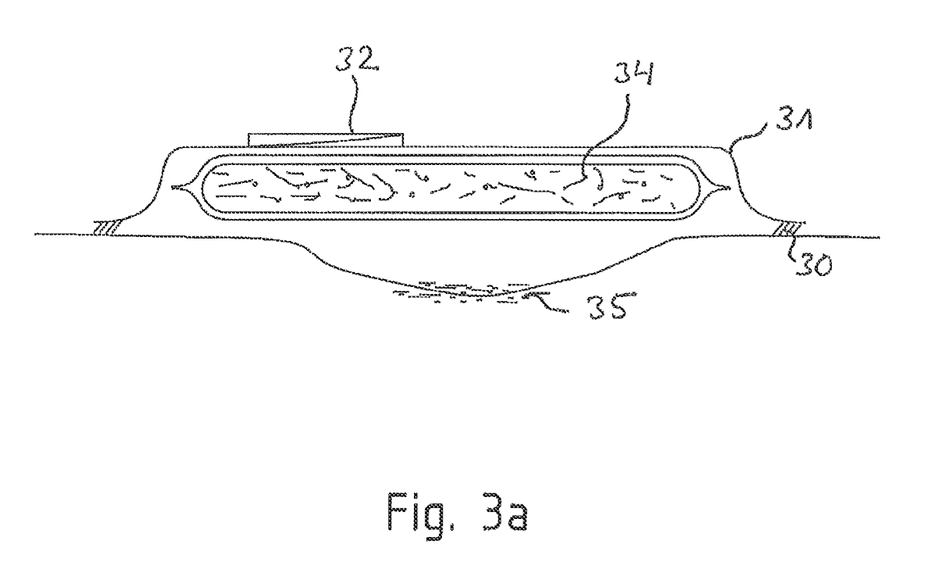

FIG. 3a shows the wound-covering article with the film-like element 31 and adhesive element 30 with which the film-like element is attached to the skin of the patient that surrounds the wound 35. The film-like element comprises a flange 32 here as prearrangement for attaching a vacuum device. In addition, an absorption body 34 in a casing is placed between the film-like element 31 and the wound 35.

Figure 3B:
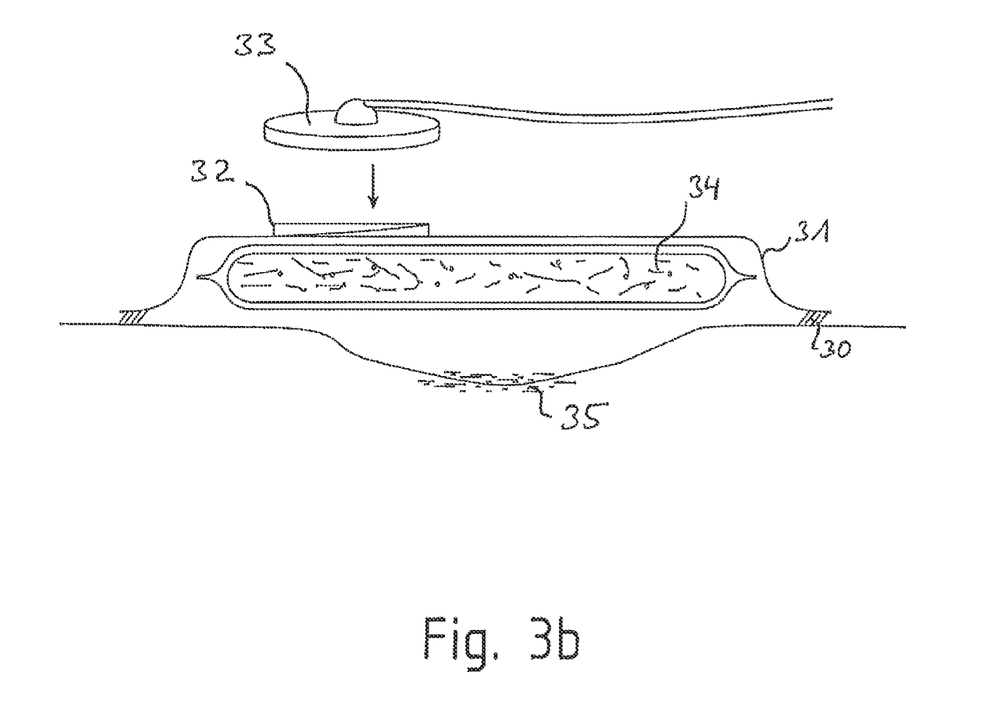

FIG. 3b shows how the flange counterpiece 33 is coupled to the flange 32 (see direction of arrow). A hose connection runs from the flange counterpiece to the vacuum device (not shown).

Figure 4A:
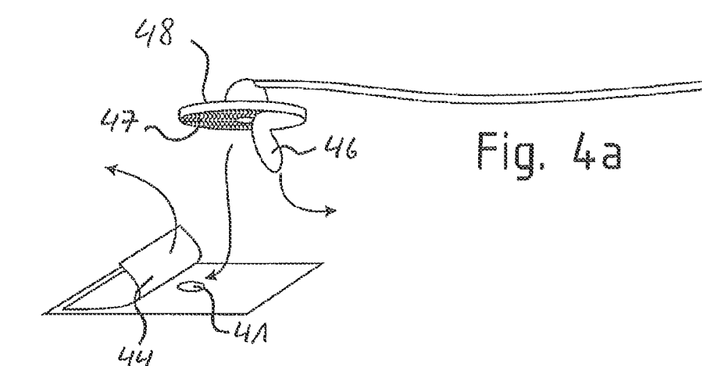
Figure 4B:
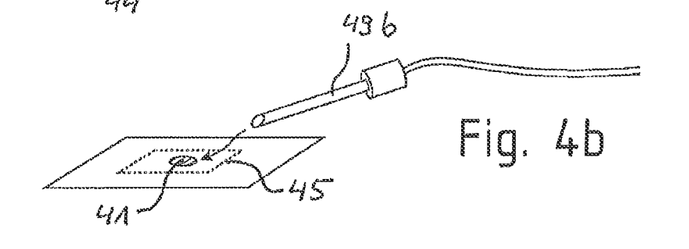
Figure 4C:
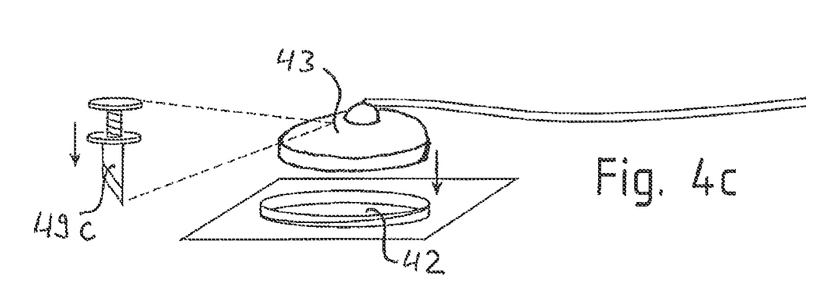
Figure 4D:
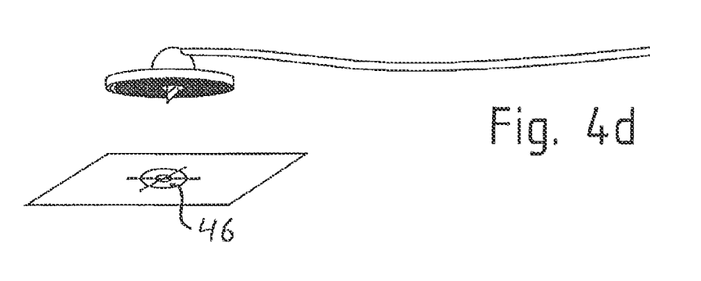

FIG. 4a to d show different variants of the prearrangement on the film-like element and possible coupling devices coordinated with them. FIG. 4a shows a prearrangement for the attachment of a vacuum device with a material recess 41 in the film-like element over which an adhesive element 44 that can be drawn off is placed. In order to open the prearrangement the adhesive element 44 is drawn off in the direction of the arrow so that the material recess 41 is now free. The coupling device 47 for the attachment of a vacuum device comprises an adhesive surface 47 with a protective film 46 that is also drawn off for the attachment to the film-like element so that the adhesive surface 47 is connected to the film-like element around the material recess 41. The connection to the vacuum device is therefore established via the coupling 48 that can be adhered. The coupling 48 that can be adhered is followed by a hose connection to the means that produces the vacuum (not shown). FIG. 4b shows another variant of the prearrangement in which the material recess 41 in the film-like element has a protective element 45 underneath it that that can be perforated. A cannula or hollow needle 49b is used as coupling device, with which the connection to the vacuum device is established by perforating the protective element 45. FIG. 4c shows a prearrangement as flange 42 on the film-like element. The flange counterpiece 43 contains a spring-suspended blade 49c in the small rubber dome which blade can be pressed down with the attachment of the flange counterpiece 43 by manual pressure on the dome in order to cut a hole in the film-like element inside the flange 42. A connection to the vacuum device (not shown) is created via the hose which also ends in the rubber dome. FIG. 4d shows a marking 46 on the film-like element on which the coupling device is placed with a cannula, hollow needle or blade for perforating the marking and therefore perforating the film-like element.

Figure 5A:
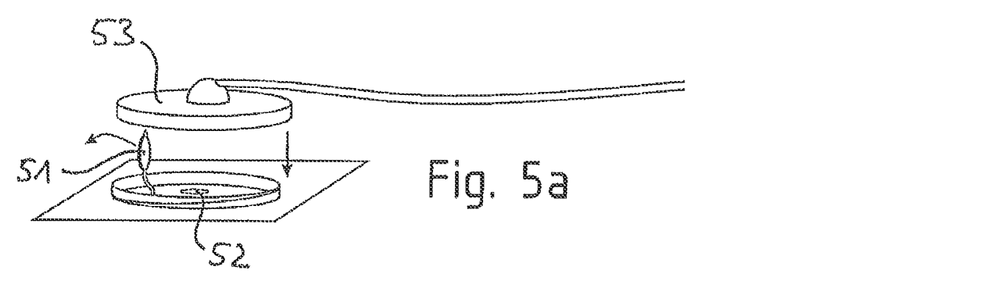
Figure 5B:
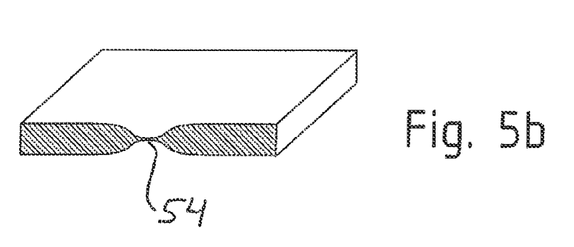

FIG. 5a shows yet another variant of the prearrangement in which an opening 52 inside a flange on the film-like element can be closed with a cover 51. The opening 52 is freed by raising the cover 51, that is constructed, e.g., as a pushbutton and that can be entirely removed or remains connected to the flange with a small safety mechanism and the flange counterpiece 53 can be attached to establish the connection. FIG. 5b shows a film-like element with a local thinning of material 54 in cross section.

Figure 6A:
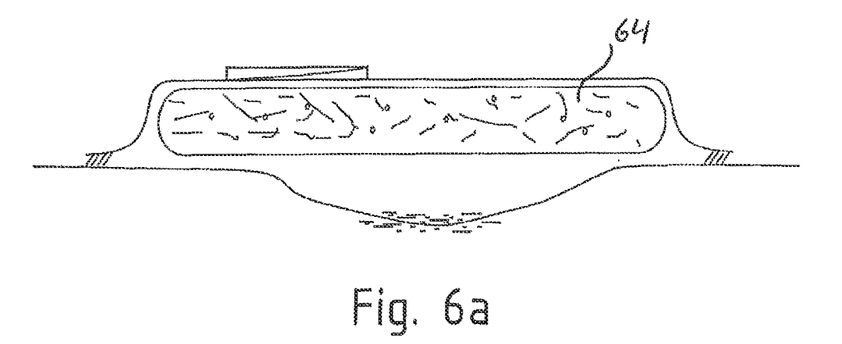
Figure 6B:
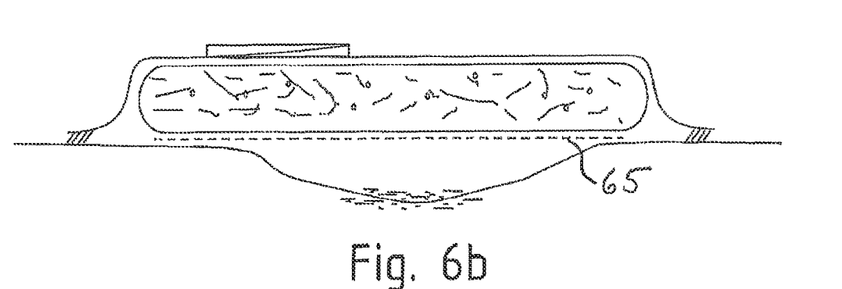
Figure 6C:
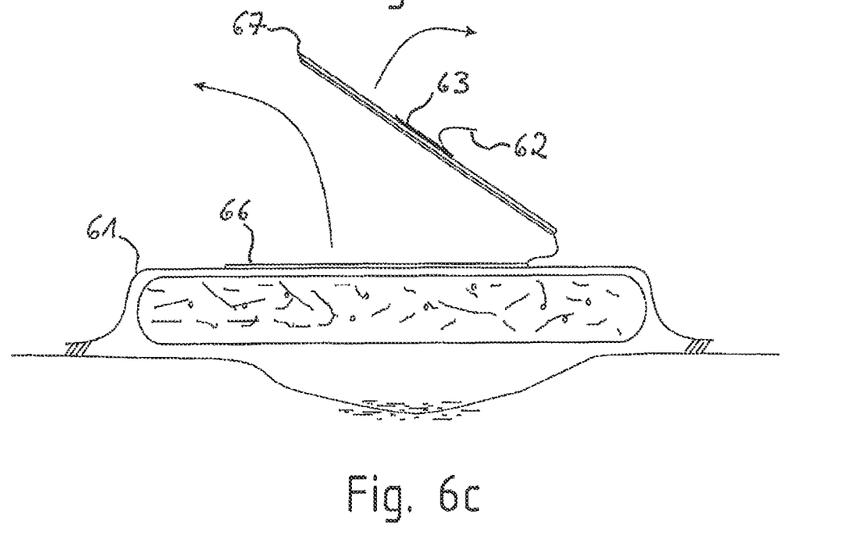

FIG. 6a shows a wound-covering article with a film-like element and prearrangement and an absorption body 64 underneath them. FIG. 6b shows a wound-covering article with a film-like element with prearrangement and as absorption body underneath them. Another layer 65 under the absorption layer is arranged inside the wound-covering article. FIG. 6c shows a wound-covering article with a film-like element 61 and an opening in the film-like element 66 through which the absorption body can be introduced or removed like through a window. The cover 67 for opening the film-like element through which the absorption body can be introduced or removed furthermore has a material recess 63 which remains closed by an adhesive element 62 until the attaching of a vacuum device.

Figure 7A:
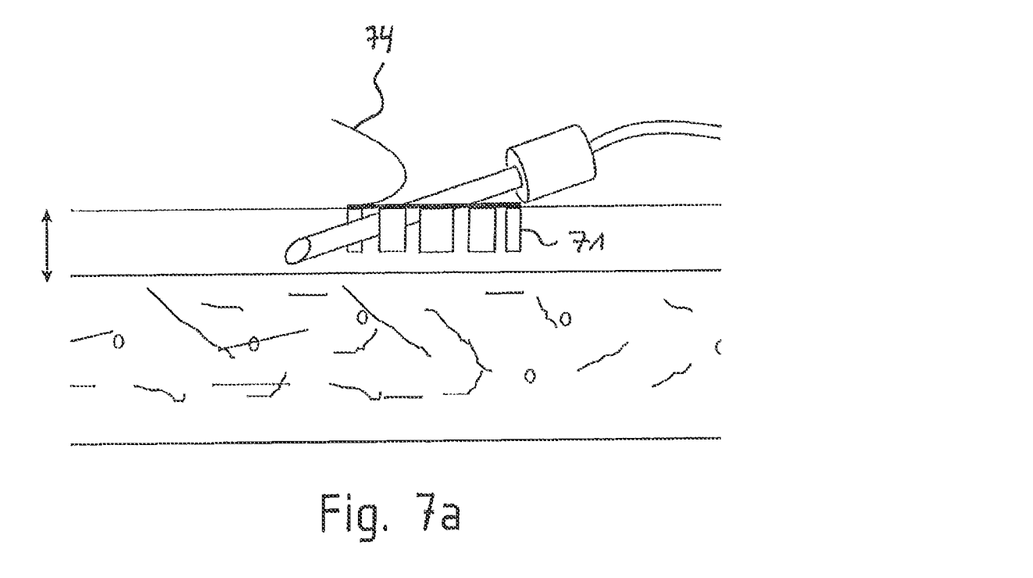

FIG. 7a shows a gear-shaped spacer 71 that is attached underneath the film-like element on the prearrangement and that prevents the hollow needle or cannula from penetrating into the absorption body when the adhesive element 74 is raised since this is prevented by the spacer 71. To the extent that the drainage is supposed to extend into the absorption body, such a spacer 71 can optionally be eliminated.

Figure 7B:
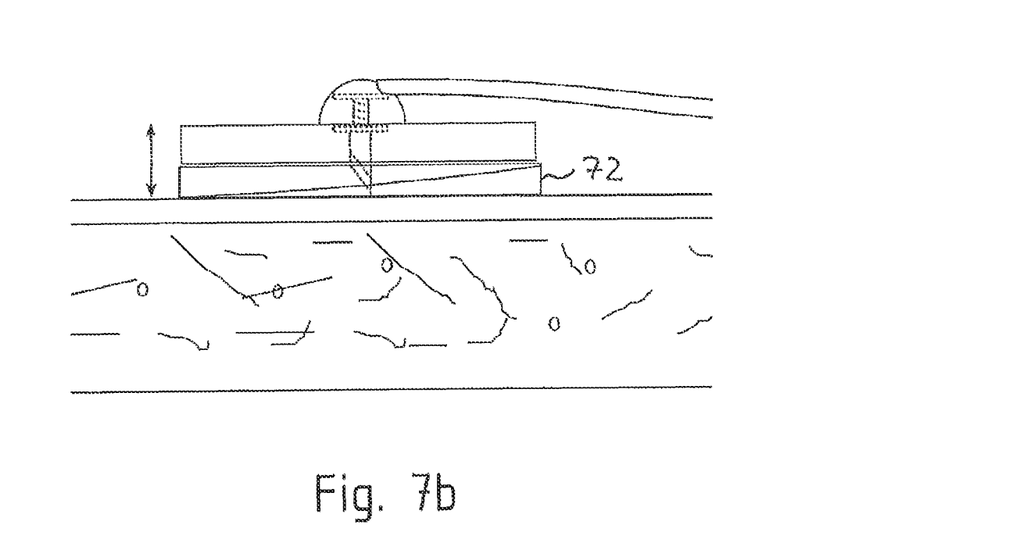

FIG. 7b shows how a safety distance to the absorption body is created by the flange system itself since the flange 72 limits the penetration depth of the knife or of the cannula in the flange counterpiece. The blade or cannula penetrates through the film-like element by a slight manual pressure on the rubber dome of the flange counterpiece but not up to the absorption body.

Figure 8A:
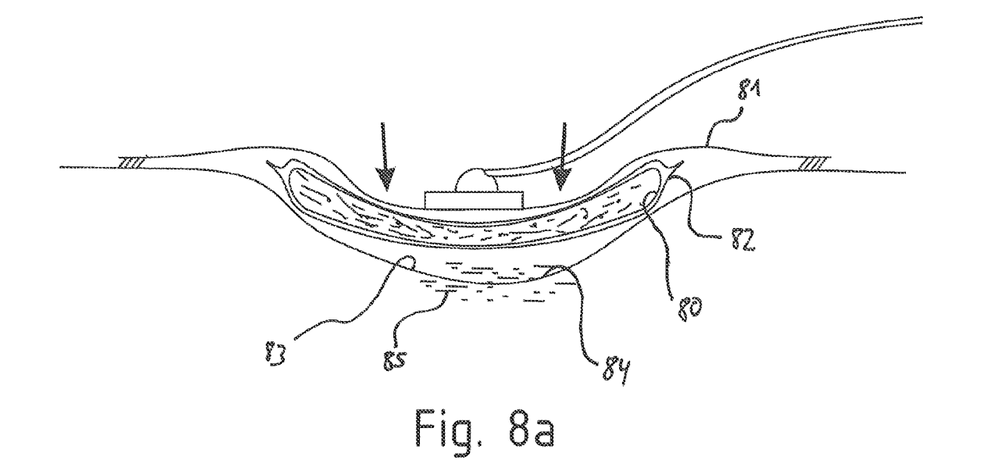

FIG. 8a shows the arrangement of the wound-care article in accordance with the invention with an absorption body 80 with an elastic, film-like element 81 and/or with an elastic casing 82 on a deep wound 83 on the wound bottom 84 of which exudate 85 is standing. In deviation from FIG. 8 the casing 82 can be an integral component of the film-like element at least in sections—for example, in the area facing away from the wound. It is ensured by the elastic, film-like element 81 and/or the elastic casing 82 that when a vacuum is applied, the absorption body can be drawn or pressed against the wound bottom 84 (indicated by the arrows) which is necessary in particular in the case of deep wounds in order to make contact in this manner with the exudate 85 to be absorbed.

Figure 8B:
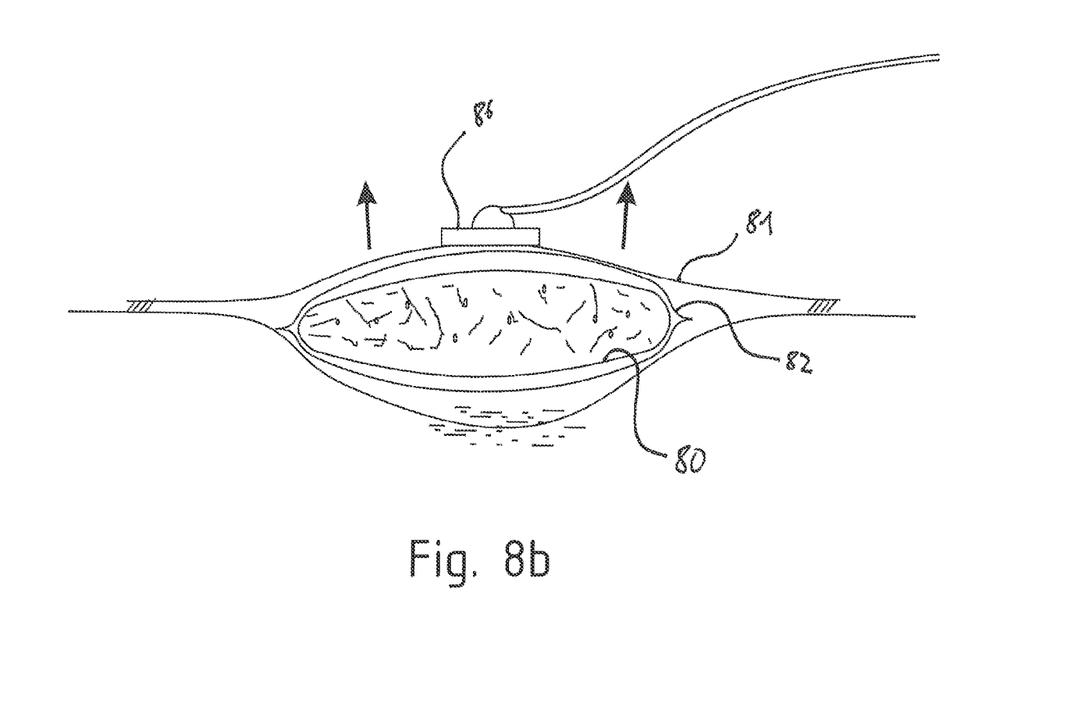

FIG. 8b shows an arrangement similar to that of FIG. 8a but at a later point in time. The absorption body 80 has already absorbed large amounts of exudate. It is ensured by the elastic, film-like element 81 and/or the elastic casing 82 that the latter do not oppose the expansion of the absorption body conditioned by the absorption of liquid. Therefore, it is ensured that the absorption body can achieve its full absorption capacity. At this point in time the coupling device 86 (and with it the vacuum device that is not shown and is connected to it) can already be decoupled or, however, the vacuum device is turned off and no longer draws any vacuum.

Therefore, it can be provided that the application of a vacuum solely serves to draw or press the absorption body against the wound bottom 84 in order to make contact in this manner with the exudate to be absorbed. As soon as this contact is made, it can be provided that the vacuum device is separated or turned off. In this case the further acquisition of exudate takes place exclusively by the absorption body.

What is claimed is:

1. A wound-covering article configured for attachment to a vacuum device, said wound-covering article comprising:
   a continuous, non-penetrated and undivided film element with reduced gas permeability that comprises a local thinning of penetrable or dividable material as a prearrangement, the local thinning of penetrable or dividable material being thinner than a portion of the film element surrounding the local thinning;
   an absorption body configured to absorb liquid from wound exudate when placed on a wound and covered with the film element, said absorption body comprising hydro-active polymers selected from the group consisting of:
   i) super-absorbing polymers (SAP) being a copolymer of acrylic acid and sodium acrylate;
   ii) fibers of modified cellulose that are capable of converting into a gel by the absorption of liquid from-the wound exudate; and
   iii) alginate fibers that are capable of converting into a gel body by the absorption of liquid from-the wound exudate; and
   a coupling device configured to connect to said prearrangement,
   said coupling device comprising a cannula, a blade, or a hollow needle for perforating the local thinning of the penetrable or dividable material to form a perforation in the local thinning for drawing a vacuum drawn on the wound using the vacuum device connected to the coupling device of the wound-covering article.

2. The wound-covering article according to claim 1, wherein the prearrangement further comprises:
   a) a marking that indicates a possible perforation position;
   b) an opening that is closed with a cover; or
   c) a flange for the coupling device.

3. The wound-covering article according to claim 1, wherein the film element is gastight or permeable by water vapor.

4. The wound-covering article according to claim 1, wherein the film element is transparent at least in sections and comprises a window opening through which material is removable from a wound area located underneath the wound-covering article when in use.

5. The wound-covering article according to claim 1, wherein the absorption body comprises at least one laminar element of foam and fleece.

6. The wound-covering article according to claim 1, wherein at least one edge of the wound covering article comprises a laminar adhesive element.

7. The wound-covering article according to claim 1, wherein the prearrangement has a spacer for limiting a depth of the cannula, blade, or hollow needle during perforation of the local thinning.

8. The wound-covering article according to claim 1, wherein the wound-covering article further comprises at least one other layer selected from the group consisting of:
   a) a wound spacing lattice;
   b) a layer with a high drying potential that drains off liquid;
   c) a layer comprising modified cellulose;
   d) a layer comprising silver or silver ions; and
   e) a layer with bonding potential for bacteria.

9. The wound-covering article according to claim 1, wherein the coupling device comprises at least one element selected from the group consisting of:
   a) a flange counterpiece;
   b) an adhesive layer; and
   c) a compressible dome.

10. A kit for wound care comprising a wound-covering article according to claim 1 and one or more elements selected from the group consisting of:
   a) a vacuum device;
   b) a vacuum hose for connecting the coupling device to the vacuum device;
   c) a filter membrane that allows gas to pass through the vacuum hose but prevents passage of liquid through the vacuum hose;
   d) a non-return valve that prevents a backflow of evacuated liquid through the vacuum hose; and
   e) a coupling for decoupling the wound-covering article the vacuum device without losing a previously established vacuum.

11. A method for treating a wound, the method comprising:
   providing a wound-covering article according to claim 1;
   placing the absorption body of the wound-covering article on the wound;
   covering the absorption body with the film element of the wound-covering article;
   connecting the coupling device of the wound-covering element to the prearrangement;
   perforating the local thinning using the cannula, blade, or hollow needle of the coupling device to form a perforation in the local thinning; and
   drawing a vacuum on the wound through the perforation in the local thinning using a vacuum device connected to the wound-covering article by the coupling device.

* * * * *